(12) United States Patent
Kumar et al.

(10) Patent No.: US 11,013,937 B2
(45) Date of Patent: May 25, 2021

(54) AUTOMATIC SELECTION OF OPTIMIZATION STRATEGY IN ITERATIVE TREATMENT PLANNING

(71) Applicant: KONINKLIJKE PHILIPS N.V., Eindhoven (NL)

(72) Inventors: Prashant Kumar, Bangalore (IN); Matthieu Frédéric Bal, Geldrop (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 393 days.

(21) Appl. No.: 16/067,861

(22) PCT Filed: Jan. 6, 2017

(86) PCT No.: PCT/EP2017/050258
§ 371 (c)(1),
(2) Date: Jul. 3, 2018

(87) PCT Pub. No.: WO2017/118725
PCT Pub. Date: Jul. 13, 2017

(65) Prior Publication Data
US 2020/0261744 A1    Aug. 20, 2020

(30) Foreign Application Priority Data

Jan. 7, 2016  (EP) .................................... 16150397

(51) Int. Cl.
*A61N 5/00*    (2006.01)
*A61N 5/10*    (2006.01)

(52) U.S. Cl.
CPC ......... *A61N 5/1038* (2013.01); *A61N 5/1077* (2013.01)

(58) Field of Classification Search
CPC ............................ A61N 5/1038; A61N 5/1077
See application file for complete search history.

(56) References Cited

U.S. PATENT DOCUMENTS

| | | |
|---|---|---|
| 8,085,899 B2 | 12/2011 | Nord et al. |
| 8,658,992 B2 | 2/2014 | Otto |
| 9,044,602 B2 | 6/2015 | Kilby et al. |
| 9,421,397 B2 | 8/2016 | Purdie et al. |

(Continued)

OTHER PUBLICATIONS

Albin Fredriksson et al. "Optimizing the Scenario Positions for Robust Radiation Therapy Treatment Planning". Oct. 10, 2012. Chapter 3.1.4.

*Primary Examiner* — Dani Fox

(57) ABSTRACT

The invention relates to a system and method for generating a radiotherapy treatment plan on the basis of treatment goals comprising optimization objectives and/or constraints. A planning unit (7) generates a first treatment plan including treatment parameters for fulfilling first treatment goals in a first optimization cycle, and a decision unit (8) receives second treatment goals and compares the first and second treatment goals to 5 determine a modification of the treatment goals, assigns to the modification a category from a plurality of predetermined categories, wherein to each category a strategy from a plurality of predetermined strategies for treatment plan generation is allocated, and instructs the planning unit (7) to generate the second treatment plan in accordance with a strategy allocated to the determined category of modifications in a second optimization cycle.

14 Claims, 2 Drawing Sheets

(56) References Cited

U.S. PATENT DOCUMENTS

| | | |
|---|---|---|
| 2008/0152085 A1 | 6/2008 | Saracen et al. |
| 2011/0272600 A1* | 11/2011 | Bert ...................... A61N 5/103 250/492.1 |
| 2013/0204067 A1 | 8/2013 | Nord et al. |
| 2016/0303398 A1 | 10/2016 | Eriksson |
| 2017/0173365 A1 | 6/2017 | Bzdusek |

* cited by examiner

AUTOMATIC SELECTION OF OPTIMIZATION STRATEGY IN ITERATIVE TREATMENT PLANNING

CROSS-REFERENCE TO PRIOR APPLICATIONS

This application is the U.S. National Phase application under 35 U.S.C. § 371 of International Application Serial No. PCT/EP2017/050258, filed on Jan. 6, 2017, which claims the benefit of European Patent Application No. 16150397.4, filed on Jan. 7, 2016. This application is hereby incorporated by reference herein.

FIELD OF THE INVENTION

The invention generally relates to a user-guided iterative planning of an external beam radiation therapy treatment of a patient. More specifically, the invention relates to a system, a method and a computer program for generating a radiotherapy treatment plan for a patient.

BACKGROUND OF THE INVENTION

In external beam radiation therapy, ionizing radiation is applied to target structures, such as tumors, within patients' bodies in order to control growth of or kill cancer cells. The radiation treatment is usually delivered in plural sessions, which are also referred to as treatment fractions in the art. In more advanced types of radiation therapy, such as so called intensity-modulated radiation therapy (IMRT), precise doses of radiation are applied to regions of the patient's body. In this respect, it is typically the goal to deliver a sufficiently high radiation dose to the target structure and to spare sensitive structures, such as organs, in the vicinity of the target structure as far as possible.

The treatment parameters for delivering the radiation and controlling the radiation treatment device are defined in a treatment plan, which is generated in a planning system. In particular, a so-called inverse planning procedure may be carried out by means of the planning system. In such a procedure, the target structure and the surrounding structures to be spared are identified and treatment goals are specified. Such treatment goals include objectives which may specify requirements for the radiation dose delivered to certain regions of the patient, which should be fulfilled, and/or constraints for the radiation doses delivered to certain regions, which must be fulfilled. Then, an optimization process is carried out to find the treatment plan which fulfills the specified treatment goals.

According to one approach for finding the final treatment plan, an operator-guided iterative optimization procedure is carried in a planning system. In this procedure, the optimization of the treatment plan is made in several optimization cycles and after each optimization cycle the operator of the planning system (typically a physician) may review the treatment plan as calculated in the respective cycle in order to check whether he is satisfied with the dose distribution resulting from this treatment plan. If this is not the case, the operator may modify the treatment goals in order to achieve a desired dose distribution, and the calculation of the treatment plan may be carried out on the basis of the modified treatment goals in the next optimization cycle. This allows for finding the best treatment plan in a kind of "trial-and-error" approach, which takes advantage of the operator's experience in order to solve the complex optimization problem of finding the optimal treatment plan for a patient.

Upon the modification of the treatment goals in one optimization cycle, the re-calculation of the treatment plan in the next optimization cycle can basically be made in such a way that information from the previous cycle (e.g. portions of the calculated treatment plan) are re-used this is also referred to as warm start herein or the re-calculation can be made without using information from the previous cycle (i.e. the treatment plan is newly generated "from the scratch")—this is also referred to as cold start herein. In principle, a warm start strategy is preferred since the complexity of the calculation to be performed in the respective optimization cycle and, thus, the computation time, is reduced when a warm start is performed. However, depending on the modifications made to the treatment goals, it is sometimes not possible to re-calculate the treatment plan in a warm start strategy in such a way that the modified treatment goals are fulfilled, or the re-calculation of the treatment plan in accordance with a warm start strategy may increase the computational complexity compared to a cold start.

US 2011/0272600 A1 discloses a system for planning irradiation of two target volumes. In the system, an overlap of the positions of radiation caused by irradiating the target volumes can be detected and the irradiation planning can be adapted accordingly. In particular, overlaps are detected which occur due to changes in the positions of the structures to be irradiated between irradiation sessions. When such overlaps are determined prior to a treatment session, the irradiation planning is adapted in order to avoid incorrect doses due to the overlap. Moreover, it is possible to recognize systematic changes during plural treatment fractions and to prepare a completely new irradiation plan in this case instead of repeatedly an existing irradiation plan.

SUMMARY OF THE INVENTION

It is an object of the present invention to allow for re-calculating a treatment plan in a user-guided iterative treatment procedure according to a strategy adapted to the modifications made to the treatment goals.

In a first aspect of the invention, a system for generating a radiotherapy treatment plan for a patient is suggested. The system is configured to optimize treatment parameters on the basis of treatment goals comprising optimization objectives and/or constraints including requirements for a radiation dose to be delivered to at least one body region of the patient. The system comprises a planning unit configured to generate a first treatment plan including treatment parameters for fulfilling first treatment goals in a first optimization cycle. Further, the system comprises a decision unit configured to receive second treatment goals and to compare the first and second treatment goals to determine a modification of the second treatment goals relative to the first treatment goals;

assign to the modification a category from a plurality of predetermined categories, wherein to each category a strategy from a plurality of predetermined strategies for treatment plan generation is allocated, determine the strategy allocated to the category assigned to the modification and to instruct the planning unit to generate the second treatment plan in accordance with the determined strategy in a second optimization cycle.

By using categories of modifications of the treatment goals in such a way, it is possible to automatically and reliably determine the optimal strategy for re-calculating the treatment plan in the new (second) optimization cycle, particularly in terms of computational complexity and computation time, upon having calculated the treatment plan in a first optimization cycle and upon having received modifications of the treatment goals made by the operator of the system.

In particular, it is possible to determine whether a warm start strategy can be applied for recalculating the treatment plan in the next optimization cycle or whether a cold start should be performed, e.g. because a warm start strategy will likely not yield a satisfying result for the treatment plan. In this respect, one embodiment of the invention provides that the predetermined strategies comprise a generation of the second treatment plan on the basis of the first treatment plan (i.e. a warm start strategy) and a generation of the second treatment plan independent of the first treatment plan (i.e. a cold start strategy).

In one embodiment, the predetermined strategies include a plurality of strategies comprising a generation of the second treatment plan on the basis of the first treatment plan, each of these strategies being allocated to a different one of the predetermined categories. This allows for selecting different warm start strategies in accordance with predefined categories of modifications, where each strategy may be adapted to the allocated category.

In one embodiment of the invention, at least some treatment goals specify requirements for a radiation dose to be delivered to a certain region of a body of the patient and at least one first predetermined category of modifications consists of modifications of the requirements for the radiation dose specified in a first treatment goal. In particular, at least one treatment goal may specify a maximum radiation dose to be delivered to the body region and/or at least one treatment goal may specify a minimum radiation dose to be delivered to the body region, and the first predetermined category may consist of a modification of the maximum or minimum radiation dose.

In a related embodiment of the invention, the strategy allocated to the first predetermined category comprises a generation of the second treatment plan on the basis of the first treatment plan. Thus, a warm start strategy is advantageously used for re-calculating the treatment plan in case of changes made to dose requirements, such as, for example, to a maximum or minimum dose to be delivered to a certain body region in accordance with a treatment objective or constraint.

In a further related embodiment, at least one first predetermined category of modifications comprises a modification of the requirements for a radiation dose to be delivered to a body region specified in a first treatment goal, which exceeds a predefined threshold, and the strategy allocated to this category comprises a re-calculation of portions of the first treatment plan, which include treatment parameters for delivering radiation to said body region. The aforementioned category particularly includes modifications of minimum or maximum dose values to be delivered to the body region according to a treatment goal, and the modification particularly exceeds the predefined threshold, when a difference between the dose values specified in the first treatment goal for the first optimization cycle and the dose values specified in the modified, second treatment goal for the second optimization cycle is greater than the threshold. In this situation, the aforementioned embodiment advantageously comprises the generation of the second treatment plan according to warm start strategy in which (only) those treatment parameter are re-optimized which control delivery of radiation to the body region specified in the treatment goals. These treatment parameters may be determined in a back-projection procedure, for example. The predetermined threshold is preferably defined relative to the radiation dose specified in the first treatment. In one embodiment, the threshold may be between 10% and 30%, particularly 20%, of the radiation dose specified in the first treatment goal.

In one embodiment of the invention, the treatment plan includes a plurality of segment portions, each segment portions corresponding to one set of concurrently used treatment parameters, and the strategy allocated to the predetermined first category comprises a re-calculation of at least one segment portions of the first treatment plan which provide for a delivery of a smaller radiation dose to the patient than other segment portions. Each segment portion may particularly correspond to a certain configuration of the radiation treatment device used for delivering radiation to the patient, particularly to a certain arrangement of the radiation beam with respect to the patient body and/or to a certain shape of the radiation beam. In accordance with such a configuration, radiation may be delivered to the patient body during a predetermined time interval, in which the radiation treatment device is controlled on the basis of the treatment parameters specified in the corresponding segment portion of the treatment plan. By modifying only those segment portions of the first treatment plan which provide for a delivery of a smaller radiation dose to the patient than other segment portions in case of minor modifications of the treatment goals, it is particularly possible to reduce the risk that the overall dose distribution resulting from the generated treatment plan is deteriorated in the calculation of the second treatment plan.

In a further embodiment of the invention, at least one category of modifications includes modifications comprising an addition of at least one objective to the first treatment goals and the strategy allocated to said category comprises a decomposition of the calculation of the second treatment plan into successive partial calculations, one partial calculation corresponding to the calculation of the first treatment plan and a further partial calculation corresponding to an optimization on the basis of the added objective. By applying such a decomposition of the calculation of the second treatment plan it is possible to decompose the overall optimization problem to a series of partial optimization problems. Hereby, the complexity of the calculation of the second treatment plan can be reduced.

A related embodiment provides that—if the modifications comprises additions of plural objectives—the aforementioned strategy comprises a decomposition of the calculation of the second treatment plan into plural successive partial calculations, each partial calculation corresponding to an optimization on the basis of one added objective, wherein an order for carrying out the partial calculations is determined on the basis of ranks assigned to the added objectives. This corresponds to a so-called lexicographic ordering procedure. The ranks assigned to the added objectives may reflect the priority of these objectives for the treatment. The assignment may be made automatically on the basis of predefined rules, or it may be made by manually by the operator of the planning system.

In a further embodiment of the invention, at least some categories of modifications include modifications comprising an addition of at least one constraint to the first treatment goals and a strategy allocated to one of said categories comprises:

generating a preliminary version of the second treatment plan on the basis of the first treatment plan;

judging whether the preliminary version of the second treatment plan satisfies the added constraint; and generating the second treatment independent of the first treatment plan, if it is judged that the preliminary version of the second treatment plan does not satisfy the added constraint.

Thus, the planning system tries to generate a new treatment plan in accordance with a warm start strategy in order to fulfill the new constraint and—as constraints must be fulfilled—it uses a cold start strategy, if the treatment plan generated in accordance with the warm start strategy does not fulfill the new constraint.

Further categories may relate to modifications of the treatment goals involving a change of the target region, i.e. the region to be primarily treated in the radiation treatment. In one related embodiment of the invention, at least one first objective specifies a requirement for the radiation dose to be delivered to a target region of a body of the patient, wherein at least one category of modifications includes modifications changing the target region, and wherein a strategy allocated to said category comprises a generation of the second treatment plan independent of the first treatment plan (i.e. a cold start strategy). Such a change of the target region may particularly include change of the delineation of this region. In that regard, the embodiment takes account of the observation that it is usually not possible to re-calculate the (second) treatment plan in accordance with a warm start strategy if the target region is changed. The requirement specified by the objective of the radiation dose may particularly include a minimum radiation dose to be delivered to the target region, for example.

In a further aspect, the invention suggests a computer program executable in a processing unit of a radiation therapy system. The computer program comprising program code means for causing the processing unit to carry out a method as described above when the computer program is executed in the processing unit.

In further aspect of the invention, a method for generating a radiotherapy treatment plan for a patient is suggested. The method comprises optimizing treatment parameters on the basis of treatment goals including optimization objectives and/or constraints including requirements for a radiation dose to be delivered to at least one body region of the patient. The method further comprises:

generating a first treatment plan including treatment parameters for fulfilling first treatment goals in a first optimization cycle;

receiving second treatment goals and comparing the first and second treatment goals to determine a modification of the second treatment goals relative to the first treatment goals;

assigning to the modification a category from a plurality of predetermined categories of modifications, wherein to each category a strategy from a plurality of predetermined strategies for treatment plan generation is allocated;

determining the strategy allocated to the category assigned to the modification and generating the second treatment plan in accordance with the determined strategy in a second optimization cycle.

It shall be understood that the system of claim 1, the method of claim 14 and the computer program of claim 15 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
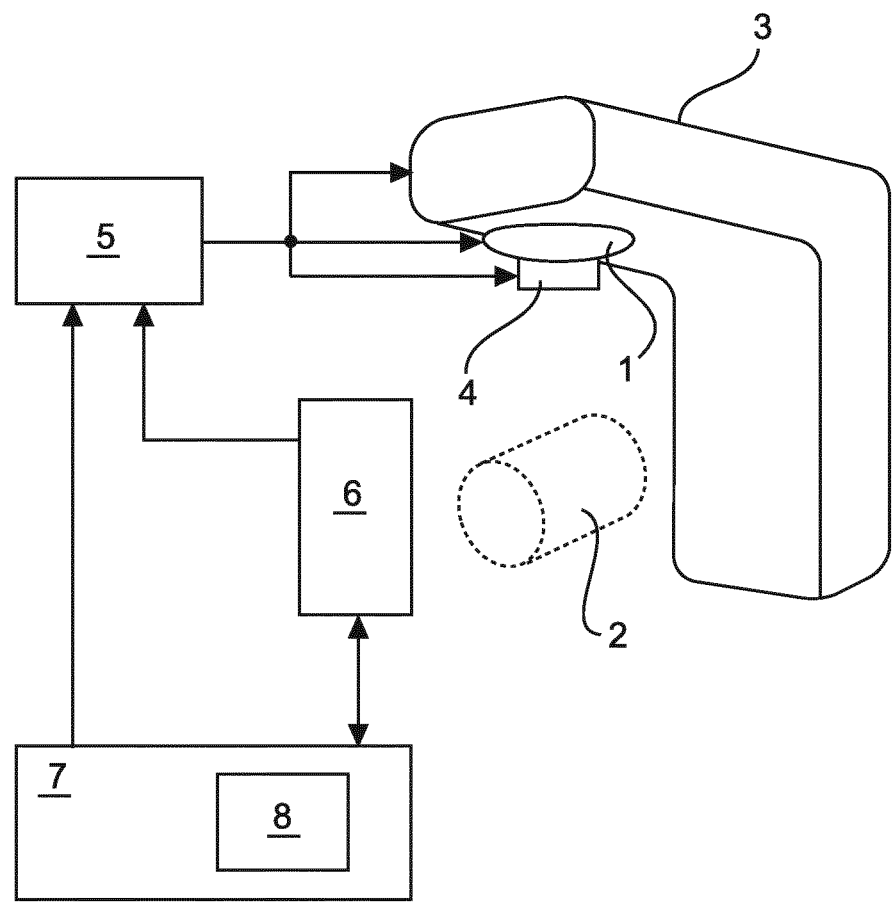
FIG. 1 schematically and exemplarily shows a radiation therapy system including a planning for generating a treatment plan, and FIG. 2 schematically and exemplarily illustrates steps of one embodiment of a method for determining an optimization strategy for re-calculating a treatment plan.

FIG. 1 schematically and exemplarily illustrates an embodiment of a radiation therapy system for delivering radiation treatments to structures within a human or animal patient body. In particular, the system may be used to treat tumors within certain structures of the body. One example of such a structure is the prostate as it is known that radiation therapy is especially suitable for treating prostate cancer.

In the illustrated embodiment, the radiation therapy system comprises a radiation source 1, which can be operated to emit ionizing radiation to be delivered to a tumor or another diseased structure within a human or animal body positioned in a treatment zone 2 of the system. For supporting the body within the treatment zone 2, the system may comprise a patient table. The relative position and orientation of the radiation source 1 with respect to the body can be varied over a certain range of positions and orientations. For this purpose, the radiation source 1 may be mounted on rotatable gantry 3 so that the radiation source 1 can be rotated around the treatment zone or body within a certain angular range, which may be 360° or less. In addition, the gantry 3 and/or the patient table may be movable back and forth in a direction parallel to the rotation axis of the gantry 3. Further, it may also be possible to rotate the patient table around an axis perpendicular to the rotation axis of the gantry 3.

The radiation source 1 may include an x-ray tube or a linear particle accelerator for producing one ionizing radiation beam; in further embodiments, the radiation system may produce several radiation beams in a similar way. The radiation source 1 is controllable in order to vary the intensity and/or energy of the radiation beam. Further, the radiation source 1 may be provided with a collimator 4 for shaping the radiation beam. The collimator 4 may particularly allow varying the radiation intensity across the radiation beam in a defined way. For this purpose, the collimator 4 may be configured as a so-called multi-leaf collimator. During delivery of the radiation treatment, the configuration of the collimator 4 is usually changed (based on the treatment plan discussed herein below) so that the radiation beam is delivered with a time-varying shape. The variation of the radiation beam is usually made in such a way that the radiation beam does not hit the entire target region within the patient body for at least some configurations of the collimator 4.

In one implementation, the radiation treatment is delivered in accordance with successive so-called segments, where each segment corresponds to a certain collimator configuration or beam shape (also referred to as segment shape herein below) and to certain (emitted) radiation dose, which may be specified in monitor units (MU). In between two segments, the collimator configuration is changed from the configuration of the first segment to the configuration of the second segment. During this period, the radiation beam may be turned off (this is usually also referred to as step-and-shoot approach). Likewise, it is possible to continuously change the collimator configuration and/or the emitted dose in accordance with the segments without interrupting the radiation beam, as it is the case in volume modulated arc therapy (VMAT), for example.

For controlling the radiation source 1, the collimator 4 and the patient table (if moveable) during the treatment (particularly for controlling the modifiable parameters of the radiation source 1, the collimator 4 and the patient table), the system includes a control unit 5. During a radiation therapy treatment, the control unit 5 controls the relative position and orientation of the radiation source 1 and the body by positioning the gantry 3 and/or the patient table. Further, the control unit 5 controls the intensity and energy of the radiation beam and the radiation beam shape. Preferably, the control unit 5 is implemented in a processor unit including a microprocessor for executing a control program comprising the control routines carried out by the control unit 5.

In addition, the radiation therapy system may comprise a localization unit 6 for localizing the structure to be treated within the patient body during a radiation treatment. In one embodiment, the localization unit 6 may include an imaging unit, which produces images of the inner of body in accordance with a suitable imaging modality. In this respect, the localization unit 6 may include an ultrasound device, a computed tomography (CT) device, a magnetic resonance imaging (MRI) device or a fluoroscopy imaging unit, for example. Such devices are known to a person skilled in the art as such and, thus, they are not described in greater detail herein. By means of such a device, the localization unit 6 produces three-dimensional images of the body region including the structure to be treated. In these images, the structure may be identified by means of a suitable pattern recognition algorithm executed in the localization unit 6.

The radiation treatment of the structure within the body may be performed during a plurality of fractions, where the fractions may be delivered to the structure on consecutive days or in another cycle. In order to deliver one fraction to the structure within the body, the body is positioned in the treatment zone 2 of the radiation therapy system at a defined position relative to the radiation source 1. Upon having positioned the body in treatment zone, the control unit 5 controls the delivery of radiation to the structure to be treated. In so doing, the control unit 5 aligns the radiation source 1 and controls the further parameters of the radiation source 1 and the collimator 4 in accordance with a treatment plan stored in the control unit 5 for the treatment of the specific patient.

The treatment plan defines the irradiation parameters for the radiation treatment of the structure. These parameters include the alignment of the radiation source 1 relative to the target region within the patient body, the collimator configurations to be used during the treatment and the radiation intensities.

For generating the treatment plan, the radiation therapy system comprises a planning unit 7. The planning unit 7 may be configured as a computer device, such as, for example a personal computer, which executes a treatment planning software for generating treatment plans which are then used by the control unit 5 for controlling the execution of the treatment fractions. In one embodiment, the planning unit 7 may be located in the vicinity of the control unit 5 and may be directly connected to the control unit 5, where the treatment plan may be transmitted from the planning unit 5 to the control unit 4 via this connection. In further embodiments, the planning unit 7 may be connected to the control unit 5 through one or more data networks, and the treatment plan may be transmitted via the network connection. Alternatively, the planning unit 7 may store the treatment plan in a suitable data recording means, and this data recording means may be transported to the control unit 7 which may then read the treatment plan from the data recording means. In the latter embodiments, the planning unit 7 may also be located remote from the control unit 5.

The generation of the treatment plan is made under the control of an operator of the planning unit 7 (which may e.g. by a physician) in accordance with an iterative procedure. In this procedure, an initial treatment plan is generated at first, which may then be modified in one or more optimization cycles.

Typically, the initial treatment plan (and the modified treatment plan) is generated on the basis of an internal image of the patient body, which is preferably a three-dimensional image that shows the target structure and that may show additional structures surrounding the target structure. As usual, the image may consist of small volume elements, which are commonly referred to as voxels, and the image may be generated using any suitable imaging modality known to a person skilled in the art, such as, for example, CT or MRI. In particular, the image may be generated using the localization unit 6 of the radiation therapy system, if the localization unit 6 comprises an imaging device. However, the image may likewise be generated using another imaging device.

In the internal image of the patient body, the target structure to be treated is identified at first. This may be done in an automated or semi-automated process, in which the contour of the target structure is delineated in the image. In addition, further structures may be identified in the image in addition to the target structure. Such further structures may particularly include critical body regions, such as organs, which are located in the vicinity of the target structure and which shall receive no radiation or a lower radiation dose than the target structure. Such structures are referred to as structures at risk herein below. For instance, if the target structure is a prostate, such structures at risk may include the bladder, parts of the intestine and bones.

In the next step, the initial treatment plan may be generated using a forward planning procedure. In such a procedure, the treatment parameters are manually specified by the operator based on his experience, or the treatment parameters are defined in a semi-automatic process in which the planning unit 7 assists the operator, e.g. by providing suggestions for the treatment parameters which may be accepted or modified by the operator. Such suggestions may e.g. be generating in accordance with a knowledge-based algorithm. After having specified the parameters, the resulting dose distribution is determined and compared with a desired dose distribution by the operator. If the differences between the distributions are too large, the treatment parameters may be modified and the dose calculation may be repeated one or several times, until the operator is satisfied with the result.

In an alternative and preferred embodiment, the initial treatment plan is generated in an inverse planning procedure. In such a procedure, the operator specifies the treatment goals at first. Then, the planning unit 7 performs an optimization procedure to determine the treatment parameters in such a way that the treatment goals are fulfilled.

The treatment goals may include treatment a set of objectives and/or treatment constraints. There may be objectives of different types which can be specified by the operator of the planning unit 7, including a minimum radiation dose to be delivered to the patient, a maximum dose to be delivered to the patient, the maximum radiation dose to be delivered to a given region of the patient's body (particularly to the target structure and/or to a structure at risk), the minimum radiation dose to be delivered to a given body region (particularly the target structure) and an indication whether a uniform radiation dose is to be delivered to a certain region (which is typically a region of the target structure). For the target structure any combination of these objectives may be specified. For a structure at risk, particularly a maximum dose delivered to given regions may particularly be specified. Further, a weight may be assigned to each objective, which may reflect its importance in the overall treatment objectives. When such weights are assigned to one or more objectives, the planning unit may calculate the treatment parameters in such a way that objectives having a higher weight are satisfied more likely than objectives having a lower weight, in case such objectives are in conflict with each other.

In addition of such objectives, constraints may be specified for generating the treatment plan. Such constraints correspond to objectives, which must not be violated during the radiation treatment.

In order to specify the objectives and constraints, the planning unit 7 may provide a suitable user interface for receiving corresponding user inputs. In particular, the planning unit 7 may provide a graphical user interface allowing the operator to delineate the target structure to be treated and structures at risk within the internal image of the patient in a manual or semi-automatic procedure. For the delineated structures and regions thereof, the operator may then specify treatment objectives and constraints as explained above. Likewise, it is possible in further embodiments that the operator specifies the objectives and constraints in another way.

On the basis of the specified objectives and constraints, the planning unit 7 calculates the treatment plan in accordance with a suitable optimization algorithm. In one possible implementation, the optimization algorithm may minimize a cost function F which is a collection of individual objective functions $F^k$, where each individual objective function $F^k$ represents one objective. In one embodiment, the cost function F may particularly correspond to a weighted sum of the objective functions $F^k$, i.e.

$$F(\tau) = \sum_{k=1}^{N} w^k F^k$$

where $\tau$ denotes the set of treatment parameters to be determined and the parameter $w^k$ denotes the weight of the objective k. As an example, the objective function representing a maximum/minimum radiation dose for a certain volume V may be given by $$F^k = \sum_{i \in V} f(d_i, d^k) \cdot \left[\frac{d_i - d^k}{d^k}\right]^2 \cdot \Delta v_i,$$

where $f(d_i, d^k) = H(d_i - d^k)$ in case a maximum dose is specified and $f(d_i, d^k) = H(d^k - d_i)$ in case a minimum dose is specified. $\Delta v_i$ denotes the volume of the voxel i, $d_i = d_i(\tau)$ is the radiation dose delivered to the voxel i when the radiation parameters $\tau$ are used, $d^k$ is the maximum/minimum radiation dose to be delivered to the volume V, and H is the Heaviside step function defined by $$H(x) = \begin{cases} 0, & x < 0 \\ 1, & x \geq 0 \end{cases}.$$

The constraints specified for optimizing the treatment parameters may be represented by a function $C(\tau)$ so that the planning unit 7 may minimize the aforementioned function $F(\tau)$ and may at the same time ensure that $$C(\tau) \geq 0$$

is fulfilled.

In order to determine the treatment parameters such that the objective function is minimized and the constraints are fulfilled, any suitable optimization algorithm may be used by the planning unit 7. In one exemplary implementation, the planning unit 7 may use the NPSOL algorithm described in P. E. Gill et al., "User's guide for NPSOL 5.0: A Fortran package for nonlinear programming", Technical Report SOL 86-6, Revised 2001. However, any other suitable algorithm known to a person skilled in the art may likewise be used.

Since the generation of the treatment plan is a complex optimization problem on the basis of a plurality of criteria (objectives and constraints), the initial treatment plan does usually not include the optimal treatment parameters and, thus, the initial treatment plan is usually not used as the final treatment plan for delivering the radiation treatment to the patient. Rather, changes may be made to the initial treatment plan in one or more operator-assisted step(s) in order to achieve a desired dose distribution which optimally covers the target structure and optimally spares the structures at risk. Thus, the final treatment plan is generated in successive calculation cycles, and in each cycle, the operator can provide changes to the treatment plan generated in the previous step in order to find the optimal treatment parameters.

In this process, one cycle may be automatically finished according to predetermined criteria. In particular, a cycle may be automatically finished when some minimum of the objective function (which may also be a local minimum instead of the global minimum to be achieved) has been determined, and or one cycle may be finished after a predetermined calculation time or (particularly if the calculation is made using a recursive procedure) after a predetermined number of calculation steps. Likewise, it is possible to finish a cycle in accordance with any other suitable criterion. Further, it may also be possible for the operator of the planning unit 7 to finish a cycle manually.

Upon completion of each cycle of the planning process, the operator of the planning unit 7 may review the dose distribution resulting from the treatment plan generated in the previous cycle in order to check whether a desired dose distribution is achieved. If the treatment plan does not result in the desired dose distribution, the operator can initiate the generation of a new treatment plan in the next cycle. In order to assist the operator in reviewing the dose distribution and assessing its quality, the planning unit 7 may also automatically assesses the quality of the treatment plan and provides corresponding indications and suggestions to the operator. Such an automatic assessment may be made by comparing the dose distribution or treatment plan with clinically approved dose distributions or treatment plans previously used for treating the same target structure.

This procedure is repeated and in each repetition cycle a new treatment plan is generated until the operator stops the process. This may be done, when a generated treatment plan results in the desired dose distribution or the operator may decide to do so for other reasons. The last treatment plan generated in this process may then be used for delivering the radiation treatment and, for this purpose, it may be provided to the control unit 5 of the radiation therapy system in a way described above. In order to initiate the generation of a new treatment plan in an optimization cycle, the operator of the planning unit 7 may modify the treatment goals which have been used in the previous cycle. The modifications of the treatment goals may include modifications of objectives and/or constraints used for calculating the treatment plan in the previous cycle, such as e.g. modifications of the values of a maximum or minimum dose or modifications of a dose value to be uniformly delivered to a certain region. Further, the modifications may include the addition or deletion of objectives and/or constraints.

For example, a new treatment plan may firstly be generated only on the basis of treatment goals ensuring that a desired dose distribution is delivered to the target structure. In particular, these treatment goals may be defined by the operator in such a way that the prescribed radiation dose is delivered to the target. Then, the operator may review the treatment plan generated on this basis in order to assess the resulting radiation doses that would be delivered to certain structures at risk in the vicinity of the target structure. If the operators determines in this process that the radiation dose that would be delivered to such structures at risk is too high, the operator may add further treatment goals in order to reduce the radiation dose delivered to the structures at risk. As a further example, situations may occur in which a generated treatment plan results in the delivery of an excessive radiation dose to a certain region of the target structure (a so-called hot spot) and in the delivery of an insufficient radiation dose to another region of the target structure (so-called cold spot). Also in this case, the operator may add further objectives and/or constraints in order to achieve a more uniform dose distribution for the target structure. Of course, these examples are neither complete nor to be understood as limiting. Rather, there may be other and/or further reasons for an operator to modify the treatment goals in the process of generating the final treatment plan.

In further embodiments, an adaptive treatment planning may be carried out in which the treatment plan is modified during the treatment in order to take account of changes of the target structure during the treatment. Such changes may particularly result from the delivery of radiation to the target in the treatment fractions preceding the modification and/or from other effects, such as, for example, a natural movement and/or deformation of the target structure. In these embodiments, one or more treatment fractions have been delivered to the patient between one optimization cycle and the next optimization cycle. Further, the re-calculation of the treatment plan may be made on the basis of a new image of the target structure acquired after the delivery of the fraction, where the new image shows the changes of the target structure. On the basis of this image, the operator may modify the previously specified treatment goals in view of the changes of the target structure. Then, a new treatment plan may be calculated as in the embodiments, in which the treatment plan is iteratively generated before the treatment is started.

An adaptive treatment planning necessarily requires an iterative optimization process and, thus, the invention can be used to advantage particularly in connection with such a treatment planning.

In order to generate a new treatment plan in one cycle, the planning unit 7 can use different strategies. In accordance with a first type of strategies, the planning unit 7 may re-use or maintain information included in the previous treatment plan. Such strategies are also referred to as warm start strategy herein. According to a further strategy, the planning unit 7 may newly calculate the treatment plan without using information from the previous treatment plan. Thus, the planning unit 7 calculates the new treatment plan from the scratch. This may basically be done in the same way as the calculation of the first treatment plan. This strategy is also referred to as cold start herein.

In principle, a warm start strategy is preferred since a warm start strategy requires less computational resources or less computation time. However, it has been found that a warm start is not possible for every modification made to the treatment goals. Therefore, the planning unit 7 comprises a decision unit 8, which determines for each cycle of the optimization process whether a warm start or a cold start is to be performed in order to generate a new treatment plan in this cycle. Preferably, the decision unit 8 is configured in such a way that a warm start is carried out if that is possible according to predetermined criteria, and that a cold start is only carried out when a warm start is not possible in accordance with the predetermined criteria. The predetermined criteria are preferably configured such that unnecessary cold starts are avoided, i.e. the criteria are preferably configured such that a warm start is carried out when the changes made by the operator allow for following this strategy.

The decision unit 8 determines in each step of the optimization procedure, whether the operator of the planning unit 7 has changed the treatment goals. This may not always be the case since the operator may review the dose distribution in one step and may decide to proceed with the optimization procedure without a change of the treatment goals (while other changes may eventually be made, such as, for example, a modification of a step size of the numerical optimization algorithm). If the decision unit 8 finds in one cycle that the treatment goals have not been changed, it controls the planning unit 7 to proceed with the optimization on the basis of the previously specified treatment goals.

In case the decision unit 8 determines that the treatment goals have been modified, it preferably categorizes the changes of the treatment goals in accordance with predefined criteria in order to assign a predefined category to each modification. Then, the decision unit 8 selects a strategy for further carrying out the optimization procedure with respect to each modification in accordance with the category determined for this modification. For this purpose, a predefined strategy may be allocated to each of the predetermined categories. This allocation may be pre-configured in the decision unit 8 and it may also be possible for the operator to adjust this allocation. Upon having determined the categories and the allocated strategies, the decision unit 8 controls the planning unit 7 to carry out the next step of the optimization procedure in accordance with the strategies.

With respect to the preferred warm start, there may be different warm start strategies, which may be selected by the decision unit 8 in accordance with allocated categories of possible modifications. As will be further described in the following, these warm start strategies may particularly differ in the way of selecting the parts of the previously generated treatment plan which are to be modified in the next optimization cycle.

Some warm start strategies may be applied in case of minor modifications of previously defined treatment goals (objectives and constraints). Such minor modifications may correspond to one predefined category of possible modifications and may particularly be determined by the decision unit 8 if only the dose value of a previously specified goal is modified by an amount which is not greater than a predetermined threshold. The threshold may be defined relative to the previously defined dose value. In particular, the threshold may be between 10% and 30% of the previously defined dose value, preferably the threshold may be 20% of the previously defined dose value.

In accordance with one warm start strategy that may be applied in case the decision unit 8 determines minor modifications of the treatment goals, the planning unit 7 may continue with the optimization algorithm as if no changes were made (i.e. no parts of the previous treatment plan are selected to be modified in the next optimization cycle). This strategy is based on the experience that in case of minor modifications the modified treatment goals may be fulfilled when a better approximation of the minimum of the (overall) cost function is calculated on the basis of unchanged input parameters of the optimization algorithm.

A further warm start strategy which may be applied in case of minor modifications of the treatment goal comprises that the decision unit 8 identifies those segments of the treatment plan, in which a lower radiation dose is delivered (i.e. emitted) than in other segments of the treatment plan. Then, the detection unit 8 control the planning unit 7 to modify the previously generated treatment plan on the basis of the modified treatment goals in such a way that modifications are only made in the identified segments (i.e. the segments in which a lower radiation dose is delivered). Other segments (i.e. those in which a higher radiation dose is delivered) are maintained unchanged under this strategy.

This warm start strategy has the advantages that only a part of the treatment plan, namely the identified segments, is refined when re-calculating the treatment plan and that these part have a smaller influence on the overall dose distribution resulting from the treatment plan. Hereby, the computational complexity of the re-calculation can be reduced, and the risk of deteriorating the overall dose distribution during the re-calculation can be reduced.

In one embodiment, the aforementioned warm start strategies may be allocated to predetermined sub-categories of the category of minor modifications. These sub-categories may be defined on the basis of different threshold values for the modified dose value, which may be defined in term of relative changes as explained above. So, the decision unit 8 may determine a first sub-category in case the change of the dose value of a previously defined treatment goals is smaller than a first threshold and it may determine a second sub-category if the change of the dose value of a previously defined treatment goal is between the first threshold and a second threshold that is greater than the first threshold. In this case, the decision unit 8 may control the planning unit 7 to apply the first warm start strategy explained above (i.e. to proceed with the optimization on the basis of the unchanged treatment goals) if the modifications of the treatment goals belong to the first sub-category, and it may control the planning unit 7 to apply the second warm start strategy explained above (i.e. to refine only the segments of the treatment plan, in which a lower radiation dose is delivered) if the modifications of the treatment goals belong to the second sub-category.

Likewise it is generally possible that the decision unit 8 is configured to select only one of the aforementioned warm start strategies in case of minor modifications.

In accordance with a further warm start strategy, the decision unit 8 may control the planning unit 7 to modify all parts of the treatment plan, which potentially contribute to the modified treatment goal. These parts particularly include such portions of the treatment plan which specify treatment parameters for delivering radiation to the body region to which the modified treatment goal refers (e.g. the body region for which the treatment goal specifies a minimum or maximum radiation dose or a uniform dose requirement). When the treatment plan defines segments as explained above, the relevant portions of the treatment plan particularly include the specifications of the segments in which radiation is delivered to the region to which the modified treatment goals refers. The relevant segments or portions of the treatment plan may be determined on the basis of a back-projection procedure. In this procedure, origins of beam parts may be determined which hit the voxels included in the relevant region and, thereupon, the portions of the treatment plan may be determined which specify the emission of radiations from such origins. In one embodiment, the selection of the relevant portions of the treatment plan may be made in the decision unit 8, and the decision unit 8 may control the planning unit 7 to modify the selected portions.

The aforementioned warm start strategy may particularly be selected by the decision unit 8 in case of major modifications of dose values of previously specified goals, particularly goals specifying a maximum or minimum radiation dose to be delivered to a certain body region or a uniform dose requirement. Such major modifications may include changes of dose values of previously defined treatment goals which are greater than the aforementioned threshold values. Thus, major modifications may include modifications which consist of changes of dose values of previously defined treatment goals and which are not classified as minor modifications.

While the aforementioned categories of changes of the treatment goals relate to a modification of dose values of previously specified treatment goals, further categories preferably include changes of the treatment goals that comprise the addition or deletion of treatment goals. Also in case such changes are made to the treatment goals, it may be possible to calculate the new treatment plan in accordance with a warm start strategy.

In case of such changes, particularly when new objectives and/or constraints are added, the decision unit 8 may determine whether the target structure region is modified according to the changes, i.e. whether the delineation of the target structure has changed. For example, this may be the case, when a new objective or constraint is added which aims at delivering a certain minimum radiation dose to a certain body region which was not subject to such an objective or constraint under the previously specified treatment goals. Preferably, a warm start strategy is only applied in case the region of the target structure is not changed. Otherwise, i.e. in case of a change of the region including the target structure, a cold start may be made. This is due the fact that the treatment plan is usually primarily generated on the basis of the target structure region so that a change of this region usually necessitates a new calculation of the treatment plan from the scratch.

If the decision unit 8 has determined that the target structure region is not changed in connection with the addition of treatment goals, the decision unit 8 may determine whether the added treatment goals are objectives or constraints. When the decision unit 8 determines that objectives have been added, it may control the planning unit 7 to re-calculate the treatment plan on the basis of a warm start strategy. In one embodiment, the strategy selected in this case may include a decomposition of the optimization problem to be solved into a sequence of partial optimization problems to be solved successively. In one related implementation, the cost function for one partial optimization problem may be used as a constraint when solving the next partial optimization problem.

In accordance with this strategy, one of the partial optimization problems may correspond to the minimizing of the cost function generated on the basis of the previously defined treatment goals. This problem has already been solved in the previous cycle of the optimization procedure and the related results obtained in this cycle may be used when re-calculating the treatment plan. One or more further partial optimization problems may correspond to the optimization of the treatment plan with respect to the one or more new objectives added by the operator of the planning unit 7. In case plural new constraints have been added, the planning unit 7 may particularly treat each added objective separately within the scope of a partial optimization problem and may optimize the treatment plan by successively solving the partial optimization problems corresponding to the added objectives in accordance with a hierarchical ranking of the added objectives. Here the partial optimization problems for higher ranked objectives may be solved prior to the partial optimization problems for lower ranked objectives so that it is more likely that the algorithm finds a solution that fulfills the higher ranked objectives. This corresponds to a so-called lexicographic ordering method.

The hierarchical ranking of the added objectives may be made automatically in the planning unit 7 or the decision unit 8 using predetermined rules. In accordance with such rules, objectives aiming at increasing the radiation dose delivered to certain body regions (which usually are included in the target structure for such objectives) may have priority (i.e. a higher rank) over objectives aiming at decreasing the radiation dose delivered to a certain body region (which usually correspond to a structure at risk). In addition or as an alternative, the hierarchical ranking may be established on the basis of the radiobiological or clinical priority of the objectives, which may be determined on the basis of the predetermined rules and/or defined by the operator of the planning unit 7. A similar hierarchical ranking may also be used for calculating the first version of the treatment plan or another preceding version (since also in this calculation a lexicographic ordering approach may be used).

Further, if the decision unit 8 determines that new constraints are added, the strategy for calculating the treatment in the next optimization cycle may correspond to a combination of a warm and a cold start. In accordance with this strategy, the decision unit 8 may control the planning unit 7 to carry out a warm start at first in the next optimization cycle. In particular, it may control the planning unit 7 to re-calculate the treatment plan in a similar way as it is done in case of major modifications of dose values of previously specified goals, i.e. it may control the planning unit 7 to modify those portions of the treatment plan, which specify treatment parameters for delivering radiation to the body region to which the new constraint refers. Then, it may be judged whether the treatment plan calculated in such a way fulfills the new constraints. If this is the case, the calculated treatment plan is used as the result of this optimization cycle. If this is not the case, the decision unit 8 may control the planning unit 7 to perform a cold start on the basis of the modified treatment goals including the new constraints.

Further categories of modifications may include the deletion of objectives and constraints. When the user provides such modifications of the treatment goals, the decision unit 8 may check whether the previously generated treatment plan fulfills the other defined treatment goals. If this is the case, the decision unit 8 may control the planning unit 7 to proceed with the optimization. In case further modifications are made in another category, the optimization may proceed in accordance with the strategy allocated to this category. In case the previously generated treatment plan does not fulfill the other (undeleted) objectives and/or constraints, the decision unit 8 may control the planning unit 7 to newly calculate the treatment plan in accordance with a cold start strategy in the next optimization cycle. The reason for applying the cold start strategy is that the deletion of objectives and/or constraints enlarges the "search space" for possible solutions of the optimization problem and, thus, allows for finding a further solution which may fulfill the treatment goals.

In case the decision unit 8 does not determine that a warm start strategy can be used in the next optimization cycle particularly in accordance with the categories of modifications described above, it may control the planning unit 7 to perform a cold start.

Figure 2:
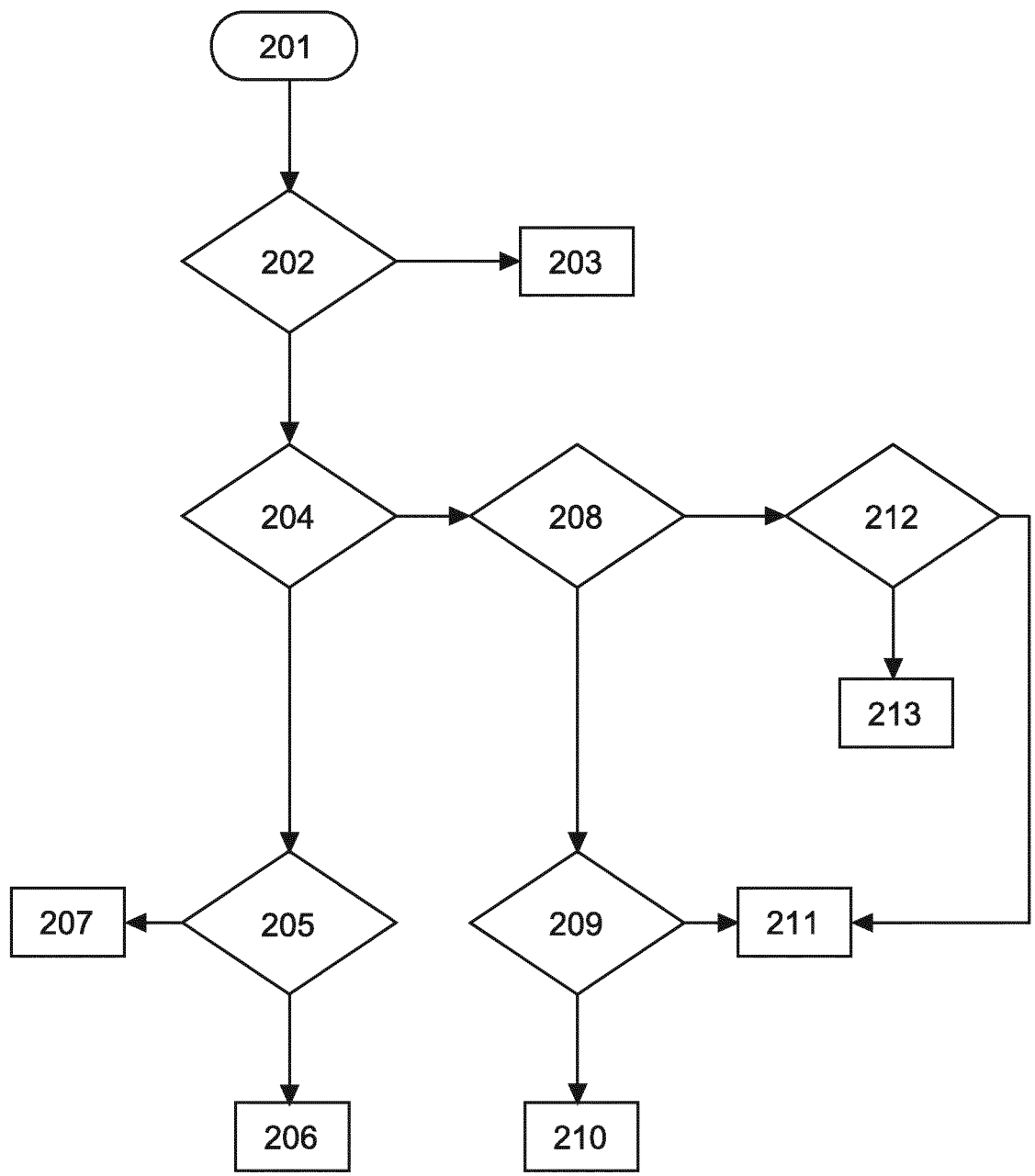

FIG. 2 schematically and exemplarily illustrates steps carried out in one embodiment of the method for controlling the re-calculation of the treatment plan in one optimization cycle. Upon the beginning of the observation cycle in step 201, the decision unit 8 checks in step 202 whether or not the operator has changed the treatment goals. If the decision unit 8 determines in step 202 that the operator has not changed the treatment goals, it instructs the planning unit 7 to proceed with the optimization on the basis of the previously defined treatment goals (step 203). Otherwise, i.e. in case the treatment goals have been modified, the decision unit 8 may check in step 204 whether the changes include modifications of dose values specified in previously defined treatment goals. If this is the case, the decision unit 8 may check in step 205 whether the changes consist of minor modifications. If the decision determines that the changes consist of minor modifications, it may control the planning unit 7 in step 206 to re-calculate the treatment plan in accordance with a warm start strategy. For this purpose, one of the warm start strategies described above for minor modifications may be applied. For selecting the warm start strategy, the planning unit 7 may optionally also determine the applicable sub-category of the minor modifications as explained above (not shown in FIG. 2). If the decision unit 8 determines in step 205 that the modifications do not consist of minor modifications, the modifications include major modifications. In this case, the decision unit 8 may control the planning unit 7 in step 207 to re-calculate the treatment plan in accordance a further warm start strategy, which may differ from the warm start strategies used in case of minor modifications. In particular, the decision unit 8 may control the planning unit 7 in step 207 to apply the warm start strategy described above for major modifications.

If the decision unit 8 determines in step 204 changes of the treatment goals which do not include a modification of dose values specified in previously specified treatment goals, it checks in step 208 whether new objectives have been added. If this is the case, the decision unit 8 may check in step 209 whether the region of the target structure is maintained as a result of the addition of the new objectives. If this is the case, the decision unit 8 may control the planning unit 7 in step 210 to re-calculate the treatment plan in accordance with a warm start strategy, for example as explained above. Otherwise, i.e. if the decision unit 8 determines in step 209 that the region of the target structure has been changed, it controls the planning unit 7 in step 211 to newly calculate the treatment plan upon a cold start.

Further, if the decision unit 8 determines in step 208 that the modified treatment goals do not consist of added objectives, the decision unit 8 may further check in step 212 whether the modified treatment goals comprise new constraints. In this case, the decision unit 8 may control the planning unit 7 in step 213 to re-calculate the treatment plan on the basis of the previously generated treatment plan at first in the next optimization cycle, and to perform a cold start in case this re-calculation results in a treatment plan which does not satisfy the added constraints.

In case the decision unit 8 determines in step 212 that the modified treatment goals do not include added constraints, objectives and/or constraints may be deleted in the modified treatment goals. In this case, the decision unit 8 may proceed to step 211 and control the planning unit 7 to perform a cold start to newly calculate the treatment plan or to proceed with the optimization in case the previously generated treatment plan fulfills the previously generated treatment goals.

Thus, in the method described above, the decision unit 8 successively checks whether the modifications of the treatment goal correspond to one of the aforementioned categories and controls the planning unit 7 to calculate the treatment plan in the new optimization cycle in accordance with the strategies assigned to the categories. In this respect, the skilled person understands that particularly the checks whether the modifications correspond to the different categories does not have to be made in the aforementioned order, but can in principle be made in any other order.

Further, the skilled person understands that other and/or further categories of modifications may be defined and that there may be a different allocation between modification categories and strategies. Moreover, the aforementioned warm start strategies are to be understood as examples of possible warm start strategies. So, other and/or further warm start strategies may be applied.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A system for generating a radiotherapy treatment plan for a patient, the system being configured to optimize treatment parameters on the basis of treatment goals comprising optimization objectives and/or constraints including requirements for a radiation dose to be delivered to at least one body region of the patient, and the system comprising:
 a planning unit configured to generate a first treatment plan including treatment parameters for fulfilling first treatment goals in a first optimization cycle, and
 a decision unit configured to
  receive second treatment goals and to compare the first and second treatment goals to determine a modification of the second treatment goals relative to the first treatment goals;
  assign to the modification a category from a plurality of predetermined categories of modifications, wherein to each category a strategy from a plurality of predetermined strategies for treatment plan generation is allocated,
  determine the strategy allocated to the category assigned to the modification and to instruct the planning unit to generate the second treatment plan in accordance with the determined strategy in a second optimization cycle,
 wherein at least one category of modifications includes modifications comprising an addition of at least one objective to the first treatment goals and wherein the strategy allocated said category comprises a decomposition of the calculation of the second treatment plan into successive partial calculations, one partial calculation corresponding to the calculation of the first treatment plan and a further partial calculation corresponding to an optimization on the basis of the added objective.

2. The system as defined in claim 1, wherein the predetermined strategies comprise a generation of the second treatment plan on the basis of the first treatment plan and a generation of the second treatment independent of the first treatment plan.

3. The system as defined in claim 2, wherein the predetermined strategies include a plurality of strategies comprising a generation of the second treatment plan on the basis of the first treatment plan, each of these strategies being allocated to a different one of the predetermined categories.

4. The system as defined in claim 1, wherein at least some treatment goals specify requirements for a radiation dose to be delivered to a certain region of a body of the patient and wherein at least one predetermined first category of modifications consists of modifications of the requirements for the radiation dose specified in a first treatment goal.

5. The system as defined in claim 4, wherein at least one treatment goal specifies a maximum radiation dose to be delivered to the body region and/or at least one treatment goal specifies a minimum radiation dose to be delivered to the body region, and wherein the first predetermined category consists of a modification of the radiation dose.

6. The system as defined in claim 4, wherein the strategy allocated to the first predetermined category comprises a generation of the second treatment plan on the basis of the first treatment plan.

7. The system as defined in claim 4, wherein at least one first predetermined category comprises a modification of the requirements for a radiation dose to be delivered to a body region specified in a first treatment goal, which exceeds a predefined threshold, and wherein the strategy allocated to this category comprises a re-calculation of portions of the first treatment plan, which include treatment parameters for delivering radiation to said body region.

8. The system as defined in claim 4, wherein at least one predetermined first category comprises a modification of the requirements for a radiation dose to be delivered to a body region specified in a first treatment goal, which does not exceed a predefined threshold.

9. The system as defined in claim 8, wherein the treatment plan includes a plurality of segment portions, each segment portion corresponding to one set of concurrently used treatment parameters, and wherein the strategy allocated to the predetermined first category comprises a re-calculation of at least one segment portions of the first treatment plan which provide for a delivery of a smaller radiation dose to the patient than other segment portions.

10. The system as defined in claim 1, wherein, if the modifications comprises additions of plural objectives, the strategy comprises a decomposition of the calculation of the second treatment plan into plural successive partial calculations, each partial calculation corresponding to an optimization on the basis of one added objective, and wherein an order for carrying out the partial calculations is determined on the basis of ranks assigned to the added objectives.

11. The system as defined in claim 1, wherein at least one category of modifications includes modifications comprising an addition of at least one constraint to the first treatment goals and wherein a strategy allocated to said category comprises:
   generating a preliminary version of the second treatment plan on the basis of the first treatment plan;
   judging whether the preliminary version of the second treatment plan satisfies the added constraint; and
   generating the second treatment independent of the first treatment plan, if it is judged that the preliminary version of the second treatment plan does not satisfy the added constraint.

12. The system as defined in claim 1, wherein at least one first objective specifies a requirement for the radiation dose to be delivered to a target region of a body of the patient, wherein at least one category of modifications includes modifications changing the target region, and wherein a strategy allocated to said category comprises a generation of the second treatment plan independent of the first treatment plan.

13. A method for generating a radiotherapy treatment plan for a patient, the method comprising optimizing treatment parameters on the basis of treatment goals including optimization objectives and/or constraints including requirements for a radiation dose to be delivered to at least one body region of the patient, and the method further comprising:
   generating a first treatment plan including treatment parameters for fulfilling first treatment goals in a first optimization cycle;
   receiving second treatment goals and comparing the first and second treatment goals to determine a modification of the second treatment goals relative to the first treatment goals;
   assigning to the modification a category from a plurality of predetermined categories of modifications, wherein to each category a strategy from a plurality of predetermined strategies for treatment plan generation is allocated;
   determining the strategy allocated to the category assigned to the modification and generating the second treatment plan in accordance with the determined strategy in a second optimization cycle,
   wherein at least one category of modifications includes modifications comprising an addition of at least one objective to the first treatment goals and wherein the strategy allocated said category comprises a decomposition of the calculation of the second treatment plan into successive partial calculations, one partial calculation corresponding to the calculation of the first treatment plan and a further partial calculation corresponding to an optimization on the basis of the added objective.

14. A computer program stored on a non-transitory medium, the computer program comprising program code means for causing the processing unit to carry out a method for generating a radiotherapy treatment plan for a patient as defined in claim 13 when the computer program is executed in the processing unit.

* * * * *